United States Patent [19]

Schlingmann et al.

[11] 4,206,243
[45] Jun. 3, 1980

[54] PROCESS FOR REDUCING THE CONTENTS OF LIPIDS AND NUCLEIC ACID IN MICROBIAL CELL MASSES

[75] Inventors: Merten Schlingmann, Kelkheim; Laslo Vertesy, Eppstein, both of Fed. Rep. of Germany

[73] Assignee: Hoechst Aktiengesellschaft, Frankfurt am Main, Fed. Rep. of Germany

[21] Appl. No.: 10,256

[22] Filed: Feb. 7, 1979

Related U.S. Application Data

[63] Continuation of Ser. No. 818,832, Jul. 25, 1977, abandoned.

[30] Foreign Application Priority Data

Jul. 27, 1976 [DE] Fed. Rep. of Germany ....... 2633666

[51] Int. Cl.² .................................................. A23J 1/18
[52] U.S. Cl. ..................................... 426/429; 426/656; 260/112 R
[58] Field of Search ......................... 426/62, 656, 429; 260/112 R; 195/4, 28 N

[56] References Cited

U.S. PATENT DOCUMENTS

| | | | |
|---|---|---|---|
| 3,615,654 | 10/1971 | Ayukawa et al. | 426/656 |
| 3,775,393 | 11/1973 | Akin et al. | 260/112 R |
| 3,781,264 | 12/1973 | Akin et al. | 260/112 R |
| 3,784,536 | 1/1974 | Akin et al. | 260/112 R |
| 3,891,772 | 6/1975 | Ridgway et al. | 426/656 X |
| 3,947,605 | 3/1976 | Chao | 426/656 |
| 4,007,088 | 2/1977 | Fencl et al. | 426/429 X |
| 4,021,303 | 5/1977 | Nakabayashi | 426/656 X |

FOREIGN PATENT DOCUMENTS

| | | |
|---|---|---|
| 121463 | 5/1976 | German Democratic Rep. |
| 1327288 | 8/1973 | United Kingdom. |
| 1400691 | 7/1975 | United Kingdom. |
| 1408845 | 10/1975 | United Kingdom. |
| 1465396 | 2/1977 | United Kingdom. |

*Primary Examiner*—Robert A. Yoncoskie
*Attorney, Agent, or Firm*—Curtis, Morris & Safford

[57] ABSTRACT

A process for reducing the content of lipids and nucleic acids in a microbial cell mass to be used for food and feeding purposes, which comprises treating the cell mass with ammonia or ammonium hydroxide and with isopropanol or an organic solvent of the formula $$R_1-(CH_2)_n-OR_2$$

wherein either $R_1$ and $R_2$ are hydrogen, and n stands for one, two or three, or $R_1$ is hydroxy, $R_2$ is hydrogen, methyl or ethyl and n stands for two or three, and, after separation of the liquid, washing the residue with water, separating the aqueous phase and drying the residue.

6 Claims, No Drawings

PROCESS FOR REDUCING THE CONTENTS OF LIPIDS AND NUCLEIC ACID IN MICROBIAL CELL MASSES

This is a continuation of application Ser. No. 818,832, filed July 25, 1977, now abandoned.

The present invention relates to a process for reducing the quantities of lipids and nucleic acid present in the cells of microorganisms. Every cell contains carbohydrates, proteins, lipids and nucleic acids. The suitability of microbial cell masses for food and feed purposes is impeded by a content of nucleic acids and lipids.

A high content of nucleic acid is serious, since it may cause pathologic effects (arthritis, urinary calculus). The presence of lipids reduces storability because they become rancid and produce an unpleasant taste.

The object of the present invention is therefore reducing the lipid and nucleic acid content of microbial cell masses.

According to known methods lipids are separated from the cell wall and membrane either by organic solvents, or they are saponified by treating them with aqueous alkalies.

A known method for separating lipids from microorganisms is carried out with mixtures of methanol and chloroform. This process is complicated and may lead to toxic by-products. Lipid extractions by means of alcohol/water/mixtures (according to German Offenlegungsschrift No. 2,405,593 or German Offenlegungsschrift No. 2,137,038 are hardly suitable for bacteria, and their technological execution is also complicated and costly.

Further known processes for reducing nucleic acid and lipid substances contained in microbial cell masses involve their separation by alkaline substances at elevated temperatures. These processes have the disadvantage that the free fatty acids formed upon hydrolysis are set free and split off together with the protein.

Moreover, part of the essential amino acids such as lysine change to a state where they cannot be used by the organism any longer.

A process has now been found for reducing the content of lipids and nucleic acids in a microbial cell mass which comprises treating the cell mass with ammonia or ammonium hydroxide and isopropanol or an organic solvent of the formula

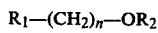

$$R_1-(CH_2)_n-OR_2$$

wherein either $R_1$ and $R_2$ are hydrogen and n stands for one, two or three, or wherein $R_1$ is hydroxy, $R_2$ is hydrogen, methyl or ethyl and n stands for two or three, and after separating the liquid, washing the residue of the cell mass with water, separating the aqueous phase and—optionally after extraction of the residual cell mass with an organic solvent of general formula I—drying it.

As microbial cell masses are preferably used microorganisms which are produced for example by cultivating on alcohol or n-paraffins in the presence of an aqueous nutrient medium and of a gas containing free oxygen. Preference is given to the use of bacteria, yeast and fungi as microorganisms.

Examples of such microorganisms include methanol utilizing bacteria of the Methylmonas family, e.g. *Methylmonas clara* ATCC 31226, or yeasts such as *Candida lipolytica* ATCC 20383 which may be obtained by cultivating on n-paraffins in the presence of an aqueous nutrient medium.

There may also be used dessicated fungus mycelium. This cell material may be provided by substrates originally used for the production of antibiotics, e.g. penicillin fermentations, after having extracted the antibiotic.

Suitable solvents of formula I are alcohols such as methanol, ethanol, n-propanol and isopropanol, preferably methanol and ethanol, especially methanol. Besides the afore mentioned alcohols are also suitable glycols and the monoethers of formula I thereof, particularly glycol and monomethyl glycol.

Ammonia is added to said solvents either as a gas ($NH_3$) or as a concentrated aqueous solution ($NH_4OH$). For making the choice, the criteria are the residual water contained in the dessicated cell material and the quantity and water content of the solvent. $NH_4OH$ is suitable for cell masses with low water content (0-15%), while $NH_3$ is more appropriate for cell masses with a higher water content (10-30%) rate.

The portion of lipids which is removed by extraction with ammonia and a solvent of formula I depends on the total water content, calculated on the quantity of solvent (in weight %), and on the $NH_3$ concentration (in weight %), calculated on the solvent.

Especially good results are obtained with a cell mass/solvent ratio of 1:3 to 1:6 with methanol and ethanol, and of 1:8 to 1:12 with propanol, glycol and the glycol monoethers. The ammonia concentration, calculated on the quantity of solvent, is 1-10 weight %, preferably 1-5 weight %. The total water quantities, provided by the cell mass, the solvent and possibly by aqueous ammonia, are 0-30 weight %, preferably 0-20 weight %, especially 0-10 weight %, calculated on the quantity of solvent.

When operating on an industrial scale, it is not necessary to dry the cells after fermentation to a minor residual water content of 4% or less. Bringing the cell mass to a dessicated cell weight such that the total water content after addition of the required quantity of solvent keeps within the optimum range is good enough. Optionally, gaseous $NH_3$ may be added to the solvent.

In order to extract the lipids, the microbial cell masses are suspended in an organic solvent of formula I and $NH_3$ is introduced or $NH_4OH$ added. It is expedient to mix the suspension thoroughly by agitation. In general, the processing temperatures range from $-20°$ to $+60°$ C., preferably from $+5°$ to $+50°$ C. and especially from $+10°$ to $+30°$ C. The processing time varies from 5 to 120 minutes and keeps preferably within 25-35 minutes. The process is, in general, carried out under normal pressure.

At the end of the treatment with solvent and ammonia, the thus obtained cell material (protein) is separated from the solvent by any suitable process such as centrifugation, filtration and sedimentation, preferably by filtration.

The solid cell material thus obtained may be treated once more with anyone of the aforementioned solvents in order to remove the lipids as completely as possible.

The residue may be dried for further removal of residual solvent and ammonia, suitably under reduced pressure, preferably from 80-150 mm Hg, and at elevated temperatures, preferably from $40°-50°$ C. The dried product thus freed from lipids is odorless.

The liquid phase separated from the solid cell material by means of the above described process contains ammonia and dissolved lipids. The solvent may be separated from the fats by distillation under reduced pressure, then recycled.

Subsequently the thus processed cell masses are introduced in water. Preferred ratios of the cell mass (in weight %) to water added are 1:1 to 1:30, especially 1:5 to 1:15. The minimum quantity of water has to allow for agitating the suspension.

The pH-value during the water treatment should keep within the range of 5–8.5, preferably 6–7.5 and is if necessary adjusted accordingly, especially in case cell masses from the first processing stage are used, which are not yet dry or not completely dry and which contain residual quantities of ammonia which may lead to too high a pH.

This extraction of nucleic acids, salts, polysaccharides and water-soluble secondary metabolites with water is generally carried out in a temperature range from 30°–95° C. under normal pressure, preferably at temperatures from 40° to 70° C., especially from 50° to 60° C. The extraction time, depending on the extraction temperature and the quantity of water, may vary from 5 to 120 minutes; good results are obtained with an extraction time from 25 to 45 minutes. For separating solid and liquid components, the suspension is centrifuged at temperatures of preferably from 10° to 30° C. Other suitable separation processes are sedimentation and filtration.

In order to facilitate the separation of the cell mass in this second extraction step up to 20 weight %, preferably from 5–15 weight %, of a lower alcohol such as ethanol, methanol, preferably of methanol are suitably added to the water.

The solid phase is freed from residual liquid by usual processes such as vacuum freeze drying, vacuum drying or spray drying. The product has an agreeable smell, a lighter color than the starting material and a particularly good water-binding ability. Due to the removal of lipids and nucleic acids, the product is especially well suited for preparing food and feed mixtures. The product according to the invention thus contains but a residue of 0.5 to 3.5 weight % of lipids and but 0.5 to 4.5 weight % of nucleic acids.

The process according to the invention avoids the disadvantages of known processes such as treatment with toxic solvents or separation by alkaline substances; especially no chlorinated hydrocarbons are required. The removal of fats, especially in case of bacteria, with mixtures of ammonia and solvents of formula I is much more complete than the removal achieved by treating the cell mass with mixtures of other solvents and water. Extreme temperature- and pH-ranges, which reduce the usability of the product, are avoided. The need of energy is inferior to that required by known processes involving separation by alkali substances. The protein content can be increased without producing large quantities of salts by neutralization.

The aqueous phase, separated from the solid cell material contains, besides other water-soluble components, the nucleic acids which may be recovered by known methods, such as precipitation in acid media, ultra-filtration, dialysis or enzyme treatment.

The following examples illustrate the invention:

EXAMPLE 1

*Methylomonas clara* ATCC 31226 was cultivated under aerobic conditions in a nutrient medium containing methanol as unique carbon source, ammonia as unique nitrogen source, phosphate, iron salts, magnesium salts and other usual trace elements. The bacteria cell mass produced during this cultivation was separated from the solution and subjected to spray drying. 100 g of this cell mass were added to 300 g of methanol. 10 g of gaseous $NH_3$ were introduced into the suspension while stirring, and thus dissolved. The temperature was maintained at 25°–35° C. by cooling. The mixture of methanol, ammonia and cell mass was agitated at 20° C. for 30 minutes.

The solid and the liquid phase was then separated by filtration and the solid residue was washed once with 300 ml of methanol. After another filtration, both filtrates were combined. This brown solution contained the lipids of the originally used starting substance. Methanol and ammonia were removed by distillation under reduced pressure (100 mm Hg, 40° C.). The residue, representing 9.5 weight % of the originally used cell material, was a dark brown, bad smelling paste, consisting of free fatty acids, glycerides, phospholipids and secondary metabolites.

The solid residue of the extracted cell mass, which had been obtained by filtration, was dried under reduced pressure (100 mm Hg) at 40° C. for 5 hours. 90 g of degreased cell mass were obtained, which were odorless and had a lighter color than the starting material.

This cell mass was suspended in 900 ml of water in order to reduce the nucleic acid content. The suspension, homogenized by agitation, had a pH of 6.9.

After raising the temperature to 55° C., agitation was continued for another 20 minutes. Cooling to 30° C. then took place and the solid and liquid phases were separated by centrifugation. The sediment thus obtained was again added to 900 ml of water and agitated at 20° C. for 10 minutes. Centrifugaton was then repeated and the sediment was dried under reduced pressure.

A yield of 65 g of cell mass was obtained. The nucleic acid content had decreased from originally 11.2% to a mere 1.5%. The dry product was odorless after moistening with water, it had a pleasant smell.

The results of the afore-described and the following examples are shown in the tables Ia and Ib.

EXAMPLE 2

The starting material was the same bacteria cell mass as described in Example 1. It was subjected to identical processing steps and conditions, with the exception however that the reactant of gaseous $NH_3$ was replaced by 30 ml of concentrated $NH_4OH$ (33%).

EXAMPLE 3

The process according to Example 2 was repeated, differing however by the use of 60 ml of concentrated $NH_4OH$ (33%).

EXAMPLE 4

While processing according to Example 2, methanol was replaced by ethanol as solvent.

EXAMPLE 5

While processing according to Example 3, methanol was replaced by glycol monomethyl ether, as a solvent.

EXAMPLE 6

While processing according to Example 2, methanol was replaced by i-propanol as a solvent.

EXAMPLE 7

A cell mass of methylomonas clara as described by Example 1 was used as starting material. 100 g of the spray-dried material were separated and degreased (15 g of NH₃) according to the description of Example 1, with the difference however that the residue was not subjected to complete dessication. The filter cake obtained after thorough vacuum filtration, having a solid matter content of 85%, was suspended in 900 ml of water. The pH was adjusted to 8.9, due to ammonia retained in the moist biomass.

The temperatures of the suspension were raised to 65° C. while agitating, and after 5 minutes the pH was adjusted to 7.2 by adding diluted hydrochloric acid. Agitation was then continued for another 15 minutes at 65° C., then cooling to 40° C. and centrifugation took place. The thus obtained sediment was dried.

EXAMPLE 8

*Candida lipolytica* ATCC 20383, a hydrocarbon-utilizing yeast species, was cultivated on n-paraffins in the presence of an aqueous nutrient medium and an oxygen-containing gas. The yeast cell mass was separated from the nutrient solution and dried.

100 g of the dry yeast cell mass were suspended at room temperature under normal pressure in 300 g of methanol and 10 g of gaseous NH₃ were added to this mixture within 15 minutes, the temperature of the suspension being maintained at 15° C. by cooling. After the gas was introduced, agitation was continued for another 20 minutes at 22° C., followed by filtration through a suction frit. The filter cake was mixed once thoroughly on the frit with 300 ml of methanol, then vacuum filtered. The two filtrates were combined. The solution had a yellow color and contained the lipids of the originally used cell material. Methanol and NH₃ were removed under reduced pressure (14 mm Hg).

The residue after the second filtration, consisting of the destroyed and degreased cells of the microorganism, was dried in a vacuum drying cabinet (100 mm Hg) at 40° C. for 5 hours. The thus obtained product exhibited a light color than the yeast cell mass originally used, and was odorless.

100 g of degreased and dried yeast were suspended in a solution of 1 liter of distilled water and 1000 ml of methanol, in order to reduce the original nucleic acid content of 7.5 weight %, calculated on the starting material. The mixture was agitated and, at a pH of 6.8, to which it adjusted itself, was heated to 50° C. for 15 minutes. Then by centrifugation it was separated into a sediment containing the yeast protein, and a liquid phase containing nucleic acid. The sediment was subjected to vacuum freeze drying after having been washed once more at room temperature.

The nucleic acid content of the dry material had diminished from the original 7.5 weight % to 0.4 weight %.

EXAMPLE 9

While processing according to Example 8, methanol was replaced by ethanol and 60 ml of NH₄OH (33%) were used instead of 10 g of gaseous NH₃.

EXAMPLE 10

Penicillium chrysogenum ATCC 10238 was cultivated aerobically according to known methods in a nutrient solution containing lactose, cornsteep liquor, phosphate, carbonate and magnesium sulfate. The mycelium remaining after separation of the thus produced penicillin, was dried and used as starting material.

The process was carried out acccording to the description of Example 8, however, NH₃ was replaced by NH₄OH (33%). The degreased dry mycelium was washed with water at 30° C.

EXAMPLE 11

The starting material was an identical cell mass as described in Example 10, however, methanol was replaced by ethanol. The temperature during the water extraction was increased to 85° C. and maintained at this level for 15 minutes.

The following Tables Ia+Ib show the results of Examples 1–11.

Table Ia

| | Removal of the lipids | | | |
| | 100 g of cell mass | | | |
| Example | type | Fat wgt. % | nucleic-acid wgt. % | solvent 300 g | NH₃ (g) or NH₄OH (33%, ml) |
|---|---|---|---|---|---|
| 1 | Methylomonas | 7 | 11.2 | methanol | NH₃ 10 |
| 2 | Methylomonas | 7 | 11.2 | methanol | NH₄OH 30 |
| 3 | Methylomonas | 7 | 11.2 | methanol | NH₄OH 60 |
| 4 | Methylomonas | 7 | 11.2 | ethanol | NH₄OH 30 |
| 5 | Methylomonas | 7 | 11.2 | glycol monomethyl ether | NH₄OH 60 |
| 6 | Methylomonas | 7 | 11.2 | i-propanol | NH₄OH 30 |
| 7 | Methylomonas | 9.6 | 15.4 | methanol | NH₃ 15 |
| 8 | Candida-lipolytica | 8.2 | 7.5 | methanol | NH₃ 10 |
| 9 | Candida-lipolytica | 8.2 | 7.5 | ethanol | NH₄OH 60 |
| 10 | dessicated mycelium | 3.5 | 2.6 | methanol | NH₄OH 30 |
| 11 | dessicated mycelium | 3.5 | 2.6 | ethanol | NH₄OH 30 |

Table Ib

| | Removal of nucleic acids | | | | |
| | Washing water | | | Cell mass obtained | | |
| Example | quantity (l) | pH | temperature (°C.) | quantity (g) | Fats wgt. % | Nucleic acid wgt. % |
|---|---|---|---|---|---|---|
| 1 | 0.9 | 6.9 | 55 | 68 | 0.8 | 1.5 |
| 2 | 0.9 | 6.9 | 60 | 67 | 1.3 | 1.2 |
| 3 | 0.9 | 7.0 | 65 | 63 | 2.0 | 1.1 |
| 4 | 0.9 | 6.9 | 50 | 67 | 2.2 | 1.5 |
| 5 | 0.9 | 7.1 | 55 | 63 | 2.8 | 2.3 |
| 6 | 0.9 | 7.0 | 60 | 64 | 3.4 | 4.0 |
| 7 | 0.9 | 7.2 | 65 | 62 | 1.2 | 1.4 |
| 8 | 0.8 | 6.8 | 50 | 68 | 1.4 | 0.4 |
| 9 | 0.8 | 6.5 | 45 | 67 | 1.8 | 0.7 |
| 10 | 0.9 | 6.5 | 30 | 78 | 1.1 | 0.5 |
| 11 | 0.9 | 6.5 | 85 | 79 | 1.3 | 0.8 |

What is claimed is:

1. A process for reducing the content of lipids and nucleic acid in a microbial cell mass, which comprises first extracting said cell mass at a temperature not exceeding 50° C. for a time from 5 minutes to 120 minutes with a liquid extractant comprising ammonia or ammonium hydroxide and isopropanol or an organic solvent of the formula $R_1-(CH_2)_n-OR_2$, wherein either $R_1$ and $R_2$ are hydrogen, and n is 1, 2, or 3, or $R_1$ is hydroxy, $R_2$ is hydrogen, methyl, or ethyl and n is 2 or 3, the $NH_3$-content of said liquid extractant being from 1 to 10 percent by weight of said organic solvent, the weight ratio of solvent to cell mass being between 3:1 and 12:1, and the total amount of water present during said extraction, as contributed by the cell mass, solvent, and ammonium hydroxide, being from 0 to 10 percent by weight of said solvent, separating the liquid extractant from the solvent-extracted microbial cell mass, and then extracting the separated solvent-extracted cell mass with water at a pH from 6 to 7.5 for a time from 5 minutes to 120 minutes, separating the water from the water-extracted cell mass, and drying the water-extracted cell mass.

2. A process as in claim 1 wherein said solvent is methanol or ethanol and the weight ratio of solvent to cell mass is between 3:1 and 6:1.

3. A process as in claim 1 wherein said solvent is propanol, glycol, or a glycol monoether and the weight ratio of solvent to cell mass is between 8:1 and 12:1.

4. A process as in claim 1 wherein said microbial cell mass is *Methylomonas clara* ATCC 31226.

5. A process as in claim 1 wherein said microbial cell mass is *Candida lipolytica ATCC* 20383.

6. A process as in claim 1 wherein said microbial cell mass is *Penicillium chrysogenum* ATCC 10238.

* * * * *